(12) United States Patent
So et al.

(10) Patent No.: US 11,257,770 B2
(45) Date of Patent: Feb. 22, 2022

(54) BIOLOGICAL INFORMATION DETECTING APPARATUS

(71) Applicant: SAMSUNG ELECTRONICS CO., LTD., Suwon-si (KR)

(72) Inventors: Wonwook So, Suwon-si (KR); Youngsik Hur, Suwon-si (KR); Yongho Baek, Suwon-si (KR); Jungchul Gong, Suwon-si (KR); Dooil Kim, Suwon-si (KR)

(73) Assignee: SAMSUNG ELECTRONICS CO., LTD., Suwon-si (KR)

( * ) Notice: Subject to any disclaimer, the term of this patent is extended or adjusted under 35 U.S.C. 154(b) by 198 days.

(21) Appl. No.: 16/679,916

(22) Filed: Nov. 11, 2019

(65) Prior Publication Data

US 2020/0168570 A1  May 28, 2020

(30) Foreign Application Priority Data

Nov. 27, 2018 (KR) .................. 10-2018-0148325

(51) Int. Cl.
*H01L 23/66* (2006.01)
*A61B 5/021* (2006.01)
(Continued)

(52) U.S. Cl.
CPC .......... *H01L 23/66* (2013.01); *A61B 5/02108* (2013.01); *H01L 23/4952* (2013.01); *H01L 23/5283* (2013.01); *H01L 24/05* (2013.01); *H01L 2223/6616* (2013.01); *H01L 2223/6672* (2013.01); *H01L 2223/6677* (2013.01); *H01L 2224/02372* (2013.01)

(58) Field of Classification Search
CPC ... H01L 2223/6677; H01L 2924/19102; H01L 25/043; H01L 25/0657; H01L 25/074; H01L 25/0756; H01L 25/117; H01L 25/0652; H01L 25/071; H01L 25/112; H01L 2225/06503–06596; A61B 5/024; A61B 5/053; A61B 5/0245; A61B 5/02444; A61B 5/1102; A61B 2562/0247
See application file for complete search history.

(56) References Cited

U.S. PATENT DOCUMENTS 7,181,975 B1 * 2/2007 Bradley ............... A61B 5/0215
361/283.1

FOREIGN PATENT DOCUMENTS

| JP | 2014-503336 A | 2/2014 |
| KR | 10-2014-0109187 A | 9/2014 |
| WO | 2012/109039 A1 | 8/2012 |

* cited by examiner

*Primary Examiner* — Tucker J Wright
(74) *Attorney, Agent, or Firm* — Sughrue Mion, PLLC

(57) ABSTRACT

A biological information detecting apparatus includes: an LC resonant pressure sensor including a resonant circuit including a capacitor and an inductor, and having a resonant frequency that changes depending on a change in external pressure applied to the capacitor; and an integrated circuit (IC) chip package including a coil type antenna radiating a radio frequency (RF) signal within a preset frequency band, wherein a change in the resonant frequency results in a change in a power transmission rate depending on a inductive coupling between the resonant frequency and a frequency of the RF signal. The IC chip package includes the coil type antenna disposed in a region overlapping the LC resonant pressure sensor in a plan view of the IC chip package.

18 Claims, 14 Drawing Sheets

(51) Int. Cl.
*H01L 23/00* (2006.01)
*H01L 23/528* (2006.01)
*H01L 23/495* (2006.01)

BIOLOGICAL INFORMATION DETECTING APPARATUS

CROSS-REFERENCE TO RELATED APPLICATION(S)

This application claims the benefit of priority to Korean Patent Application No. 10-2018-0148325 filed on Nov. 27, 2018 in the Korean Intellectual Property Office, the disclosure of which is incorporated herein by reference in its entirety.

TECHNICAL FIELD

The present disclosure relates to a biological information detecting apparatus.

BACKGROUND

With development of digital technologies, various portable electronic devices such as a mobile communications terminal, a smartphone, a tablet personal computer (PC), and a wearable device have been widely used. Recently, these electronic devices have been configured to have a biological information detection function of detecting biological information of a user in order to expand the functions of the electronic devices.

As a representative example of the biological information detecting method, a heart rate of a user may be measured by using a heart rate monitoring sensor. Such a heart rate monitoring sensor is implemented by an optical sensor, and a method, in which a light emitting unit (for example, a green or red light emitting diode (LED)) and a light receiving unit are combined, and the light emitting unit of the heart rate monitoring sensor outputs light in a state in which the electronic device is attached to the body of the user, and the light receiving unit measures the heart rate by using an amount of the output light reflected from a part of the body of the user and received, has been used.

SUMMARY

An aspect of the present disclosure may provide a biological information detecting apparatus using an LC (inductor and capacitor) resonance principle in order to measure a heart rate based on a bio-signal.

According to an aspect of the present disclosure, a biological information detecting apparatus may include: an LC resonant pressure sensor including a resonant circuit including a capacitor and an inductor, and having a resonant frequency that changes depending on a change in external pressure applied to the capacitor; and an integrated circuit (IC) chip package including a coil type antenna radiating a radio frequency (RF) signal within a preset frequency band, wherein a change in the resonant frequency results in a change in a power transmission rate depending on a matching rate between the resonant frequency and a frequency of the RF signal. The IC chip package may include the coil type antenna disposed in a region overlapping at least a portion of the LC resonant pressure sensor in a plan view of the IC chip package, a connection structure including a redistribution layer connected to the coil type antenna, and an IC chip disposed on one surface of the connection structure, connected to the redistribution layer, and configured to detect biological information on the basis of the change in the power transmission rate.

According to another aspect of the present disclosure, a biological information detecting apparatus may include: an LC resonant pressure sensor including a resonant circuit including a capacitor and an inductor, and having a resonant frequency that changes depending on a change in external pressure applied to the capacitor; and an IC chip package including an antenna radiating a RF signal within a preset frequency band, wherein a change in the resonant frequency results in a change in a power transmission rate depending on a matching rate between the resonant frequency and a frequency of the RF signal. The IC chip package may include a frame having first and second surfaces opposing each other and having a cavity, a connection structure disposed on the first surface of the frame and including a redistribution layer, an IC chip accommodated in the cavity, connected to the redistribution layer, and detecting biological information on the basis of the change in the power transmission rate, and an encapsulant encapsulating the IC chip and covering the second surface of the frame, and the antenna is disposed on at least one of the connection structure or the first surface of the frame, and connected to the redistribution layer.

BRIEF DESCRIPTION OF DRAWINGS

The above and other aspects, features, and advantages of the present disclosure will be more clearly understood from the following detailed description taken in conjunction with the accompanying drawings, in which.

DETAILED DESCRIPTION

Hereinafter, exemplary embodiments of the present disclosure will now be described in detail with reference to the accompanying drawings.

Figure 1:
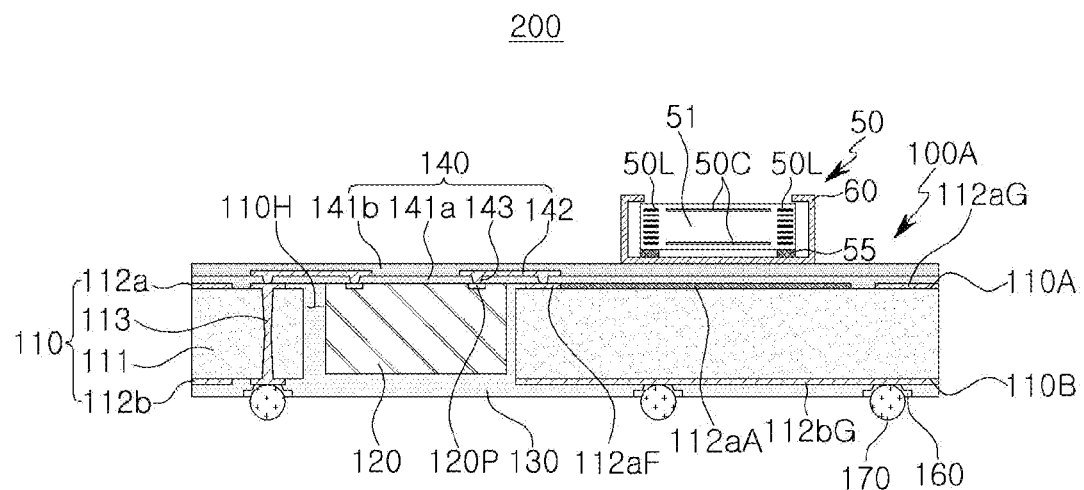
FIG. 1 is a cross-sectional view illustrating a biological information detecting apparatus according to an exemplary embodiment in the present disclosure.

FIG. 1 is a cross-sectional view illustrating a biological information detecting apparatus according to an exemplary embodiment in the present disclosure.

Referring to FIG. 1, a biological information detecting apparatus 200 according to the present exemplary embodiment may include an LC resonant pressure sensor 50 including a resonant circuit including a capacitor 50C and an inductor 50L, and an integrated circuit (IC) chip package 100A including an antenna pattern 112aA disposed in a region overlapping the LC resonant pressure sensor 50 in a plan view of the IC chip package 100A.

The LC resonant pressure sensor 50 used in the present exemplary embodiment may have a resonant frequency determined by the resonant circuit including the capacitor 50C and the inductor 50L, and the resonant frequency may be changed depending on a change in external pressure applied to the capacitor 50C. Here, the external pressure, which refers to a pressure with biological information, may mean a pressure caused by a blood flow with information such as a heart rate. A detailed description thereof will be provided later (see FIGS. 5, 6A, and 6B).

For example, the LC resonant pressure sensor 50 may have a chip structure including a main body 51, and conductive patterns disposed on the main body 51 and constituting the capacitor 50C and the inductor 50L. Such a chip structure may be a microelectromechanical system (MEMS) structure in which an applied pressure may be transferred. In the present exemplary embodiment, the LC resonant pressure sensor 50 may be embedded in a housing 60 by using a support 55 and mounted on the IC chip package 100A. The plan view of FIG. 2 illustrates an example of arrangement of the conductive patterns of the LC resonant pressure sensor 50 having the chip structure.

Figure 2:
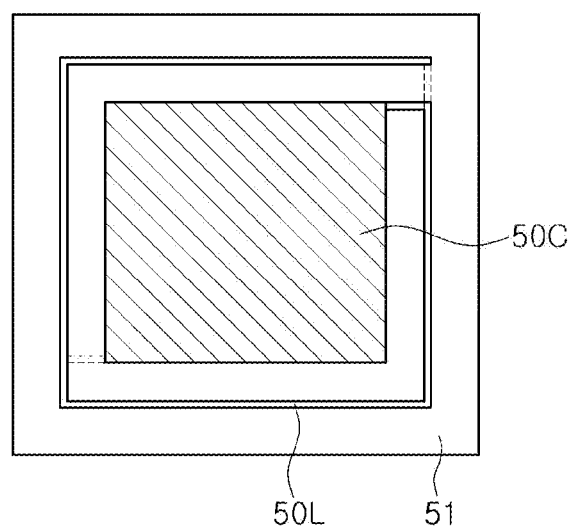
FIG. 2 is a plan view illustrating an LC resonant pressure sensor used in the biological information detecting apparatus of FIG. 1.

Referring to FIG. 2, the LC resonant pressure sensor 50 may include the inductor 50L formed of patterns having a coil structure in the main body 51, and the capacitor 50C disposed inwardly of the inductor 50L, connected to the inductor 50L, and formed of two patterns overlapping each other. In this arrangement, the capacitor 50C having a large area may be disposed at the center of a surface (corresponding to a surface illustrated in FIG. 2) to which the pressure is applied, such that the pressure is appropriately transferred to the capacitor 50C, thereby inducing a change in resonant frequency.

The IC chip package 100A used in the present exemplary embodiment may include the antenna pattern 112aA disposed on a first surface 110A of a frame 110, a connection structure 140 including a redistribution layer 142 connected to the antenna pattern 112aA, and an IC chip 120 disposed on one surface of the connection structure 140 and connected to the redistribution layer 142.

The antenna pattern 112aA may include a coil type pattern, and may receive power from the IC chip 120 to radiate a radio frequency (RF) signal within a preset frequency band. The antenna pattern 112aA may be disposed to overlap the LC resonant pressure sensor 50 in a plan view of the IC chip package 100A to radiate the RF signal to the LC resonant pressure sensor 50. The antenna pattern 112aA may include a coil pattern. The coil type antenna pattern 112aA may be designed so that a frequency thereof almost coincides with a specific value (for example, a minimum value) of the resonant frequency which varies. A matching rate between the frequency of the RF signal and the resonant frequency may be changed as the resonant frequency is changed, and a power transmission rate of power transmission by inductive coupling with the RF signal may be changed accordingly. The IC chip 120 may detect biological information applied to the LC resonant pressure sensor 50 (particularly, the capacitor 50C) on the basis of the change in a power transmission rate.

Hereinafter, a heart rate measuring process using the biological information detecting apparatus according to the present exemplary embodiment will be described in detail with reference to FIGS. 5 through 9 (an example of measurement of a heart rate).

Figure 5:
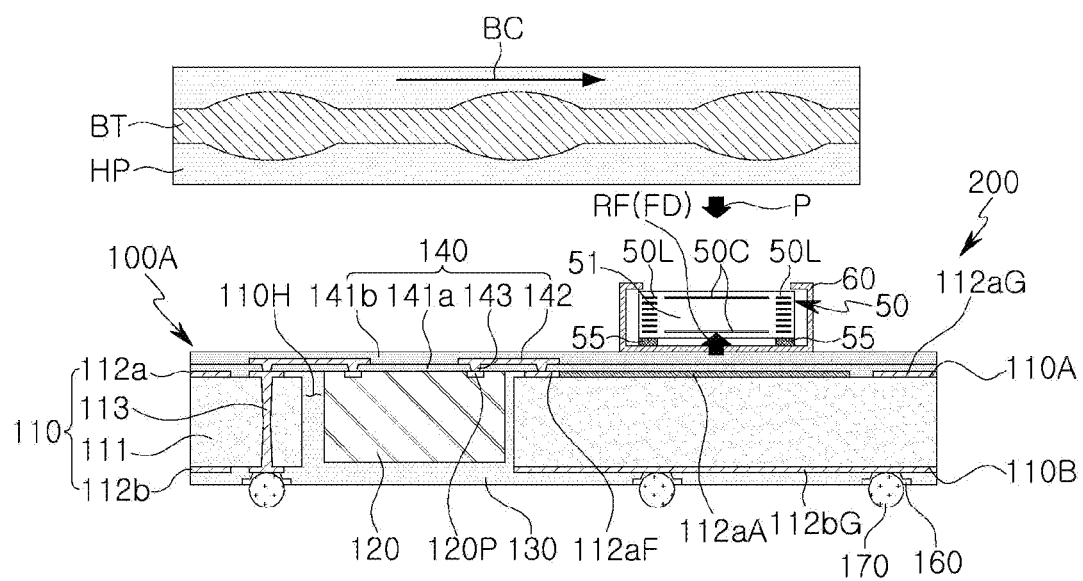
FIG. 5 is a schematic view illustrating a heart rate measuring process using the biological information detecting apparatus of FIG. 1.

FIG. 5 is a schematic view illustrating a heart rate measuring process using the biological information detecting apparatus of FIG. 1.

Referring to FIG. 5, the biological information detecting apparatus 200 of FIG. 1 is disposed so that a measurement surface of the LC resonant pressure sensor 50 is in contact with a human body HP as a measurement target.

A pressure P may be changed at the time of dilation and constriction of a blood vessel BT inside the skin of the human body HP according to a blood flow BC, and such a change in pressure P may be measured by using the LC resonant pressure sensor 50. As described above, a resonant frequency of the LC resonant circuit of the LC resonant pressure sensor 50 may be changed depending on the change in pressure at the time of dilation and constriction of the blood vessel BT.

In detail, a change in capacitance depending on an applied pressure in the LC resonant pressure sensor 50 will be described with reference to FIGS. 6A and 6B.

Figure 6A:
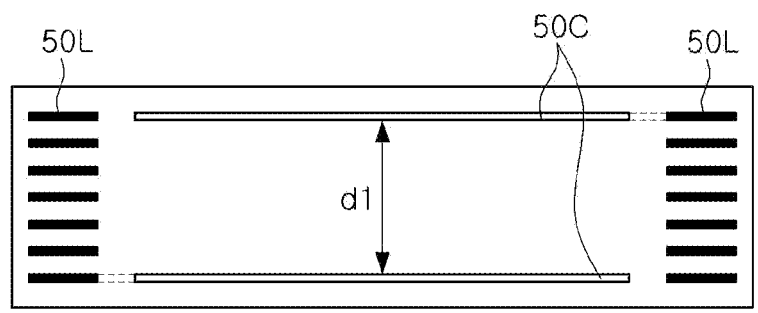
FIGS. 6A and 6B are schematic cross-sectional views illustrating a change in capacitance depending on an applied pressure in the LC resonant pressure sensor.
Figure 6B:
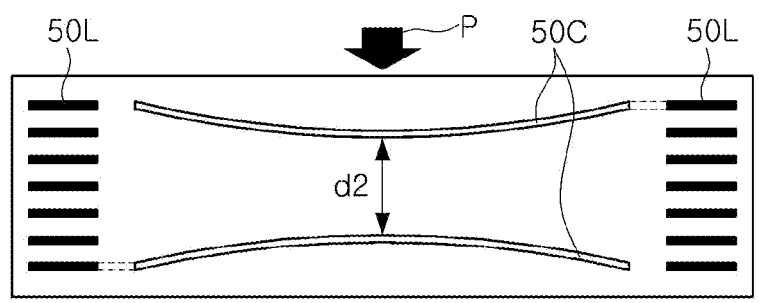

In an initial state in which a pressure is not applied as illustrated in FIG. 6A, the capacitor has a first capacitance C1 defined by an interval d1 between very thin electrode patterns of the MEMS structure, whereas, in a case in which the pressure P is applied as illustrated in FIG. 6B, an interval d2 between the very thin electrode patterns is small, such that the capacitor has a second capacitance C2 larger than the first capacitance C1. As a result, as represented by the following Equations, a resonant frequency F1 after the pressure is applied is larger than a resonant frequency F2 before the pressure is applied.

$$F1 = \frac{1}{2\pi\sqrt{LC_1}}$$

$$F2 = \frac{1}{2\pi\sqrt{LC_2}}$$

In an actual process of measuring a heart rate after the initial state (no pressure is applied), a process in which the blood vessel is dilated (pressure is applied)→the blood vessel is constricted (pressure is applied)→the blood vessel is dilated (pressure is applied)→the blood vessel is constricted (pressure is applied) is repeatedly performed. An interval d0 between the electrode patterns when the blood vessel is constricted is larger than the interval d1 when the pressure is not applied, and thus a capacitance of the capacitor is decreased, such that the resonant frequency of the LC resonant pressure sensor has the minimum value (F0) (see FIG. 7).

Figure 7:
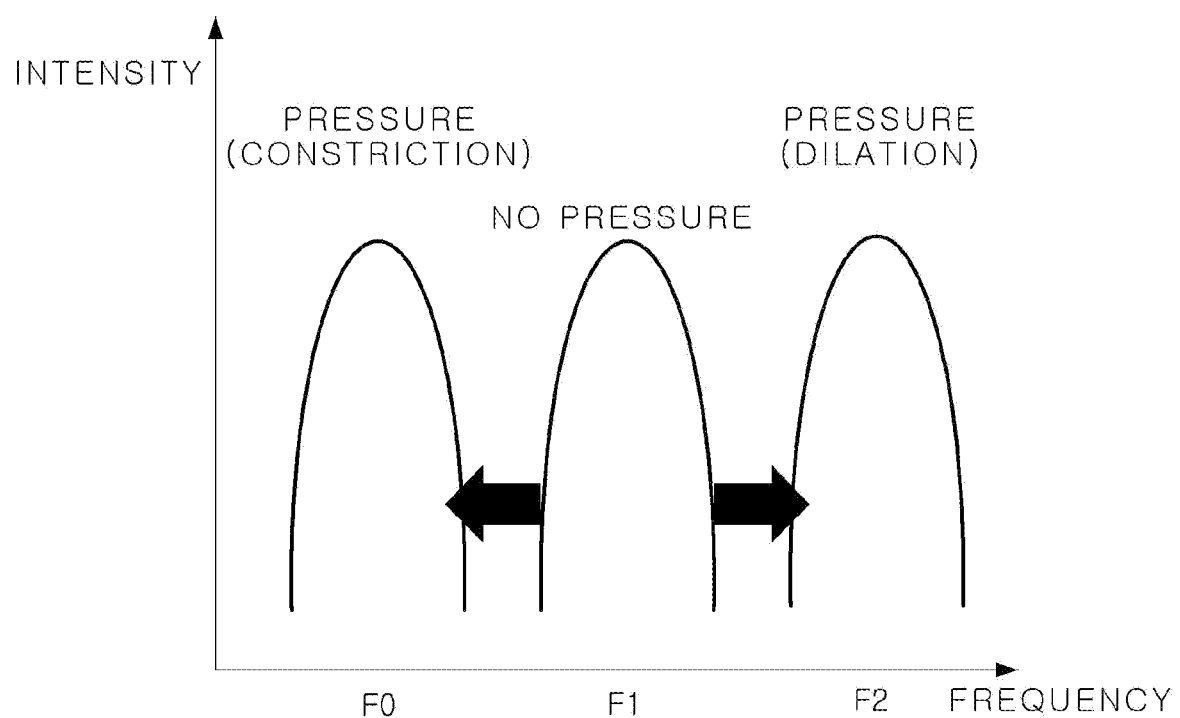
FIG. 7 is a graph illustrating a change in resonance frequency depending on an applied pressure in the LC resonant pressure sensor.

As illustrated in FIG. 7, the resonant frequency may have a value of F1 in the initial state (no pressure is applied). However, in an actual process in which the heart beats periodically, that is, in a process in which dilation and constriction of the blood vessel are repeated, the LC resonant pressure sensor 50 may have a resonant frequency F2 or F0 which is larger or smaller than the resonant frequency in the initial state (F0<F1<F2).

As the heart beats periodically, the resonant frequency of the LC resonant pressure sensor 50 may be periodically changed, and in this process, when an RF signal with a specific frequency (F0) is transmitted from the antenna pattern 112aA of the IC chip package 110A to the LC resonant pressure sensor, a power transmission rate of power transmission by inductive coupling with the RF signal may be determined according to the matching rate between the frequency of the RF signal and the resonant frequency.

Figure 8:
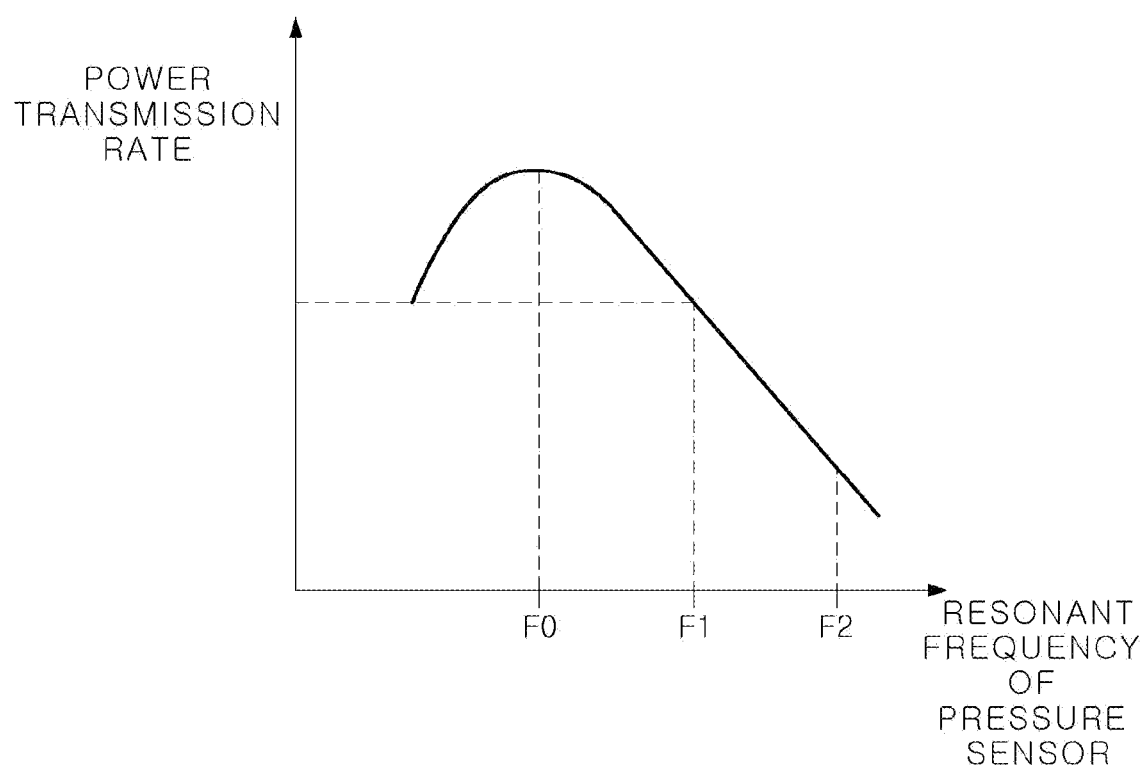
FIG. 8 is a graph illustrating a change in a power transmission rate depending on a change in resonance frequency in the LC resonant pressure sensor.

As illustrated in the graph of FIG. 8, in a case in which the LC resonant pressure sensor 50 has the resonant frequency of F0 (constriction of the blood vessel), the matching rate between the resonant frequency and the frequency of the RF signal radiated from the antenna is high, such that the power transmission rate of the RF signal may be almost maximum. However, in a case in which the LC resonant pressure sensor 50 has the resonant frequency of F2 (dilation of the blood vessel), the matching rate between the resonant frequency and the frequency of the RF signal is low, such that the power transmission rate of the RF signal may be relatively low.

Figure 9:
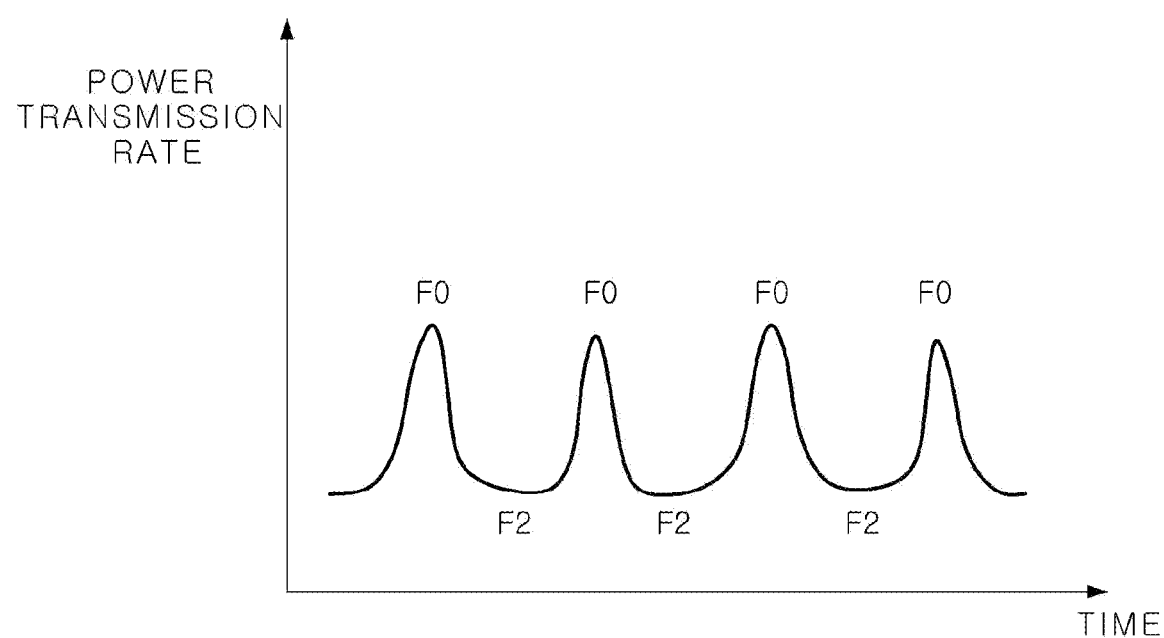
FIG. 9 is a graph illustrating a change in a power transmission rate depending on heartbeat in a predetermined period.

Such a change in a power transmission rate within a predetermined period may be detected and plotted as illustrated in a periodic graph of FIG. 9.

Referring to FIG. 9, each peak may be understood as indicating a power transmission rate based on the resonant frequency (F0) at the time of constriction of the blood vessel, and each valley may be understood as indicating a power transmission rate based on the resonant frequency (F2) at the time of dilation of the blood vessel. As such, the heartbeat causes a certain vibration (pressure: P) and a change in a power transmission rate of the RF signal within a predetermined period may be counted, thereby performing a function of detecting the heart rate by detecting peaks corresponding to the heart rate. The series of processes illustrated in FIGS. 8 and 9, that is, the process (for example, peak counting) in which the power transmission rate is measured and the change in a power transmission rate within the predetermined period is analyzed may be performed by a processor included in the IC chip 120.

As described above, the IC chip package 100A used in the present exemplary embodiment may continuously radiate an RF signal in a predetermined frequency band through the antenna pattern 112aA overlapping the LC resonant pressure sensor 50 in a plan view of the IC chip package 100A, a resonant frequency of the LC resonant pressure sensor 50 is changed depending on biological information based on a pressure such as heartbeat, and the IC chip 120 may effectively detect biological information such as a heart rate by measuring a change in a power transmission rate obtained by using the antenna pattern 112aA based on the changed resonant frequency of the LC resonant pressure sensor 50.

Hereinafter, the structure of the IC chip package 100A used in the present exemplary embodiment will be described in more detail with reference to FIGS. 1, 3 and 4.

Figure 3:
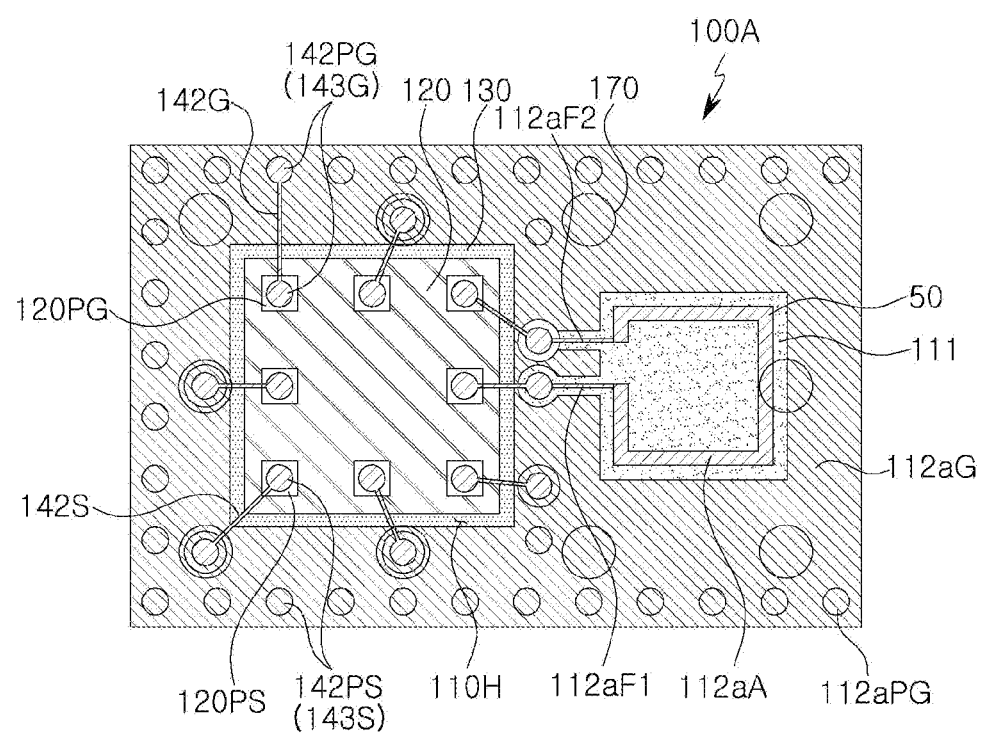
FIGS. 3 and 4 are, respectively, a plan view and a bottom view illustrating an integrated circuit (IC) chip package used in the biological information detecting apparatus of FIG. 1.
Figure 4:
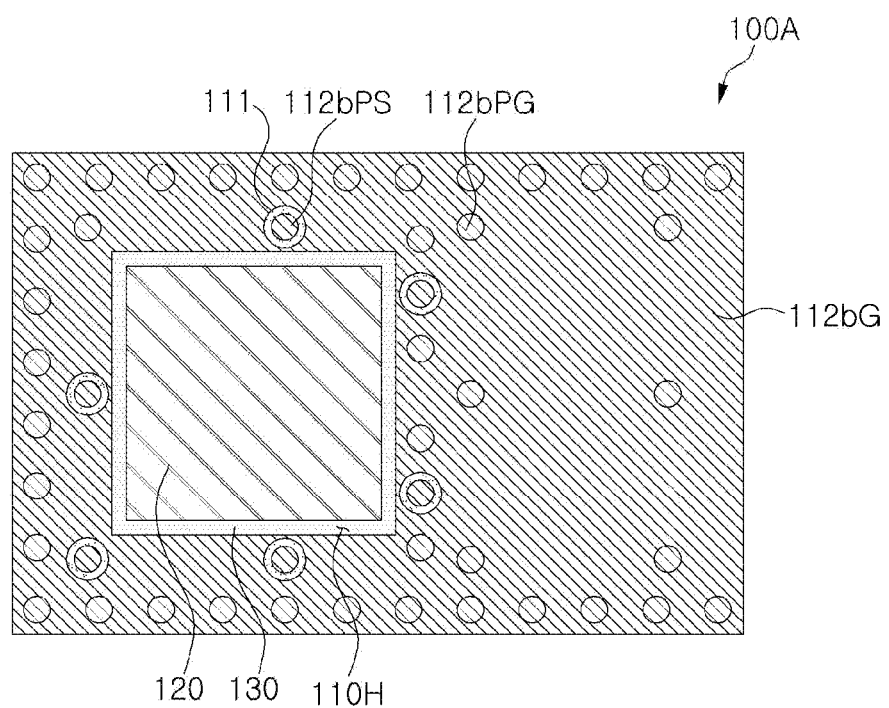

Referring to FIGS. 1, 3, and 4, the IC chip package 100A used in the present exemplary embodiment may further include the frame 110 having a cavity 110H in which the IC chip is accommodated, and an encapsulant 130 encapsulating at least portions of the frame 110 and the IC chip 120. The IC chip package 100A may include the connection structure 140 disposed on a first surface 110A of the frame 110 and an active surface of the IC chip 120.

The IC chip 120 may include a connection pad 120P connected to the redistribution layer 142, and may be disposed in a face-up form so that the active surface is directed toward the top in the drawings. The frame 110 may include an insulating layer 111, first and second wiring layers 112a and 112b disposed on opposite surfaces of the insulating layer 111, and a via 113 connecting the first and second wiring layers 112a and 112b to each other. In the present exemplary embodiment, the antenna pattern 112aA may be disposed on the same level as the first wiring layer 112a, and a ground pattern 112bG may be disposed on the same level as the second wiring layer 112b. That is, the first wiring layer 112a disposed on the first surface 110A of the frame 110 may include the antenna pattern 112aA, and the second wiring layer 112b disposed on a second surface 110B of the frame 110 may include the ground pattern 112bG.

As illustrated in FIG. 3, the antenna pattern 112aA may be connected to the redistribution layer 142 through first and second feeding lines 112aF1 and 112aF2 in a signal manner to be thus connected to the connection pads 120P of the IC chip 120 in a signal manner. An underbump metal layer 160 and an electrical connection metal 170 may be disposed beneath the frame 110, and the IC chip package 100A may thus be mounted on an external device such as a mainboard. A resonant frequency and a bandwidth of the antenna pattern 112aA may be determined according to a ground surface, a dielectric material, and a feeding line, in addition to a design of the antenna pattern.

The IC chip package 100A used in the present exemplary embodiment may include the antenna pattern 112aA and the ground patterns 112bG disposed on opposite surfaces of the frame 110. Therefore, a distance between the antenna pattern 112aA and the ground pattern 112bG may be stably secured to maintain radiation characteristics of the antenna 112aG, and a size of the antenna pattern 112aA may be reduced by using a dielectric constant of a dielectric in the frame 110, that is, the insulating layer 111, to thereby reduce a size of the IC chip package 100A.

The frame 110 may include the first and second wiring layers 112a and 112b redistributing the connection pads 120P of the IC chip 120 to thus simplify the redistribution layer 142 of the connection structure 140. In some exemplary embodiments, rigidity of the IC chip package 100A may be improved depending on a material of the insulating layer 111 constituting the frame 110, and thickness uniformity of the encapsulant 130 may be secured. The IC chip package 100A may also be utilized as a package-on-package (PoP) type package. The IC chip 120 may be disposed in the cavity 110H of the frame 110 to be spaced apart from the frame 110 by a predetermined distance. Side portions of the IC chip 120 may be surrounded by the frame 110.

As described above, the frame 110 may include the insulating layer 111, the first wiring layer 112a disposed on an upper surface of the insulating layer 111, the second wiring layer 112b disposed on a lower surface of the insulating layer 111, and a via 113 penetrating through the insulating layer 111 and connecting the first and second wiring layers 112a and 112b to each other.

A material of the insulating layer 111 of the frame 110 is not particularly limited, and may include, for example, a thermosetting resin such as an epoxy resin or a thermoplastic resin such as a polyimide resin. In some exemplary embodiments, the material of the insulating layer 111 may be a resin in which the thermosetting resin or the thermoplastic resin is impregnated together with an inorganic filler in a core material such as a glass fiber (or a glass cloth or a glass fabric), for example, prepreg, Ajinomoto Build-up Film (ABF), FR-4, Bismaleimide Triazine (BT), or the like.

Thicknesses of the first and second wiring layers 112a and 112b of the frame 110 may be greater than that of the redistribution layer 142 of the connection structure 140. Since the frame 110 may have a thickness similar to or greater than that of the IC chip 120, the first and second wiring layers 112a and 112b may be formed to have large sizes through a substrate process according to a scale of the frame 110. On the other hand, the redistribution layer 142 of the connection member 140 may be formed to have a small size through a semiconductor process for thinness.

The first and second wiring layers 112a and 112b may redistribute the connection pads 120P of the IC chip 120. The first and second wiring layers 112a and 112b may include specific patterns such as the antenna pattern 112aA as in the present exemplary embodiment. In other exemplary embodiments (see FIGS. 10 through 12), the antenna pattern may also be configured as a part of the redistribution layer 142. For example, the first and second wiring layers 112a and 112b may include copper (Cu), aluminum (Al), silver (Ag), tin (Sn), gold (Au), nickel (Ni), lead (Pb), titanium (Ti), or alloys thereof. The first and second wiring layers 112a and 112b may perform various functions depending on designs of the corresponding layers.

For example, the first and second wiring layers 112a and 112b may include ground (GND) patterns, power (PWR) patterns, signal (S) patterns, and the like.

In detail, as illustrated in FIGS. 3 and 4, the first wiring layer 112a may include the antenna pattern 112aA and the first and second feeding lines 112aF1 and 112aF2 connecting the antenna pattern 112aA to the connection pads 120P of the IC chip 120. The antenna pattern 112aA may be connected to connection pads 120PS for a signal of the connection pads 120P through signal patterns 142S of the redistribution layer 142 in a signal manner. The first wiring layer 112a may include a ground pattern 112aG having a plate shape, a pad 112aPG for a ground connection, a pad 112aPS for a signal connection, and the like. The second wiring layer 112b may include the ground pattern 112bG. The ground pattern 112bG may be connected to connection pads 120PG for a ground of the connection pads 120P through a ground pattern 142G of the redistribution layer 142. The ground pattern 112bG may be formed in a plate shape, and may occupy most of the lower surface of the insulating layer 111. The ground pattern 112bG may serve as a ground of the antenna pattern 112aA, the IC chip 120, various signal patterns, and the like. The second wiring layer 112b may include electrical connection structure pads 112bPS for a signal connection, electrical connection structure pads 112bPG for a ground connection, and the like, in addition to the ground patterns 112bG.

The via 113 may electrically connect the first and second wiring layers 112a and 112b disposed on different layers to each other, thereby providing an interlayer electrical path in the frame 110. The via 113 may include a via 113S for a signal connection, a via 113G for a ground connection, and the like. For example, the via 113 may include copper (Cu), aluminum (Al), silver (Ag), tin (Sn), gold (Au), nickel (Ni), lead (Pb), titanium (Ti), or alloys thereof. The via 113 may be completely filled with the conductive material, or the conductive material may be formed along a wall surface of a via hole. In addition, the via 113 may have any known shape such as a sandglass shape, a cylindrical shape, and the like.

The IC chip 120 may be a radio frequency integrated circuit (RFIC) including a processor having a biological information detecting function such as heart rate measurement described above. The IC chip 120 may include a body having various circuits, and the connection pad 120P may be formed on an active surface of the body. The body may be formed on the basis of, for example, an active wafer. In this case, a base material of the body may be silicon (Si), germanium (Ge), gallium arsenide (GaAs), or the like. The connection pad 120P may electrically connect the IC chip 120 to other components (for example, the redistribution layer 142). A material of the connection pad 120P may be, for example, aluminum (Al).

The IC chip 120 is disposed in a face-up form so that the active surface on which the connection pad 120P is disposed is directed toward the top in the drawings, such that a length of the antenna pattern 112aA to the first and second feeding lines 112aF1 and 112aF2 may be significantly decreased. As a result, insertion loss may be reduced.

The encapsulant 130 may be provided as an insulating portion for protecting the IC chip 120, an encapsulation form is not particularly limited and it is sufficient that the encapsulant 130 encloses at least a portion of the IC chip 120. As in the present exemplary embodiment, the encapsulant 130 may cover the second surface 110B of the frame 110, and a side surface and an inactive surface of the IC chip 120. In addition, the encapsulant 130 may fill at least a portion of the cavity 110H. For example, the encapsulant 130 may include an insulating material such as ABF, and in some exemplary embodiments, the encapsulant 130 may include a photo imageable encapsulant (PIE).

The connection structure 140 may redistribute the connection pad 120P of the IC chip 120. The connection structure 140 may include a first insulating layer 141a, the redistribution layer 142 disposed on the first insulating layer 141a, a via 143 disposed in the first insulating layer 141a and connecting the redistribution layer 142 to patterns disposed on another layer, and a second insulating layer 141b disposed on the first insulating layer 141a and covering the redistribution layer 142. For example, the first insulating layer 141a may include a photosensitive insulating material such as a photo imageable dielectric (PID) resin. In a case of using the PID resin, the first insulating layer 141a may have a smaller thickness, and a fine pitch of the vias 143 may be achieved more easily. In some exemplary embodiments, the multiple first insulating layers 141a may be formed, and may include the same material or different materials. When the multiple first insulating layers 141a are formed, the first insulating layers 141a may be integrated with each other in a case of using the same material, such that a boundary therebetween may also not be apparent. Meanwhile, the second insulating layer 141b may be provided as a passivation layer as the outermost layer of the connection structure 140. For example, the second insulating layer 141b may include an insulating material such as ABF, but is not limited thereto.

The redistribution layer 142 may serve to redistribute the connection pads 120P of the IC chip 120, and a material of the redistribution layer 142 may be, for example, copper (Cu), aluminum (Al), silver (Ag), tin (Sn), gold (Au), nickel (Ni), lead (Pb), titanium (Ti), or alloys thereof. The redistribution layer 142 may perform various functions depending on designs of corresponding layers. For example, the redistribution layer 142 may include a ground line 142G, a signal line 142S, and the like as described above. In addition, the redistribution layer 142 may include a pad 142PG for a ground, a pad 142PS for a signal, and the like.

The via 143 may be provided as an interlayer electrical path in the connection structure 140, which electrically connects the redistribution layer 142 and the first wiring layer 112*a* formed on different layers to each other. For example, the via 143 may include copper (Cu), aluminum (Al), silver (Ag), tin (Sn), gold (Au), nickel (Ni), lead (Pb), titanium (Ti), or alloys thereof. The via 143 may be completely filled with the conductive material, or may be formed in various forms such as a form in which the conductive material is formed along only a wall of the via. The via 143 used in the present exemplary embodiment may also include a via 143G for a ground, a via 143S for a signal, and the like.

The underbump metal layer 160 may be configured to improve connection reliability of the electrical connection metal 170 to improve board level reliability of the IC chip package 100A. In the present exemplary embodiment, the underbump metal layer 160 may be connected to various pads 112*b*PG and 112*b*PS of the second wiring layer 112*b* exposed through openings of the encapsulant 130. The underbump metal layer 160 may be formed in the openings of the encapsulant 130 by the known metallization method using the known conductive material such as a metal, but is not limited thereto.

The electrical connection metal 170 may be configured to physically or electrically externally connect the IC chip package 100A. For example, the IC chip package 100A may be mounted on a mainboard of an electronic device through the electrical connection metal 170. The electrical connection metal 170 may include a low melting point metal, for example, a solder including tin (Sn)-aluminum (Al)-copper (Cu) alloys, or the like. However, this is only an example, and a material of the electrical connection metal 170 is not particularly limited thereto. The electrical connection metal 170 may be a land, a ball, a pin, or the like. The electrical connection metal 170 may have a multilayer or single layer structure. When the electrical connection metal 170 has a multilayer structure, the electrical connection metal 170 may include a copper (Cu) pillar and a solder. When the electrical connection metal 170 has a single layer structure, the electrical connection metal 170 may include a tin-silver solder or copper (Cu). However, this is only an example, and the electrical connection metal 170 is not limited thereto. The number, an interval, a disposition form, and the like, of electrical connection metals 170 are not particularly limited, but may be sufficiently modified depending on design particulars by those skilled in the art. For example, the electrical connection metal 170 may be provided in an amount of several tens to several millions according to the number of connection pads 120, or may be provided in an amount of several tens to several millions or more or several tens to several millions or less.

At least one of the electrical connection metals 170 may be disposed in a fan-out region. The fan-out region refers to a region except for a region in which the IC chip 120 is disposed. A fan-out package like the IC chip package 100A used in the present exemplary embodiment may have excellent reliability as compared to a fan-in package, may implement a plurality of input/output (I/O) terminals, and may facilitate a 3D interconnection. In addition, as compared to a ball grid array (BGA) package, a land grid array (LGA) package, or the like, the fan-out package may be manufactured to have a small thickness, and may have price competitiveness.

The biological information detecting apparatus according to the present exemplary embodiment may be implemented in various forms. First, the IC chip package used in the detecting device may be variously modified depending on arrangement of antenna patterns (see FIGS. 10 through 13C).

Figure 10:
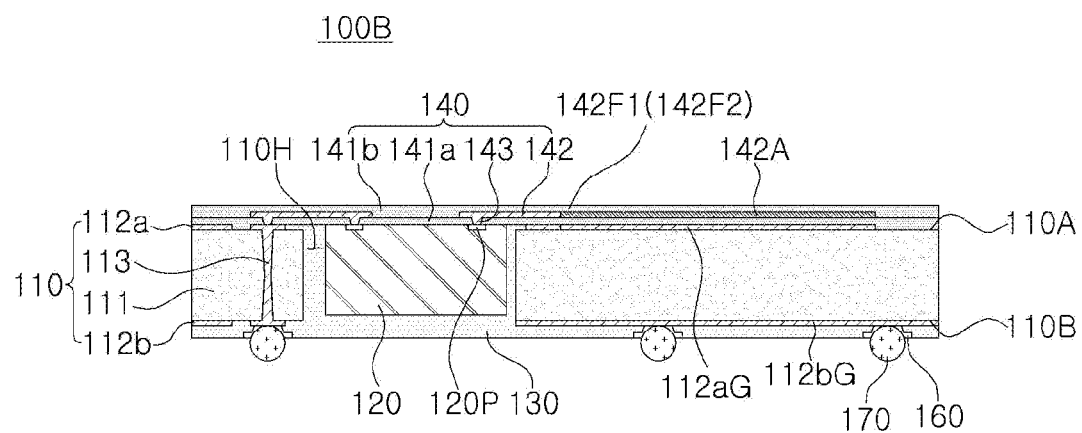
FIGS. 10, 11A, 12A, and 13A are cross-sectional views illustrating various IC chip packages that may be used in the biological information detecting apparatus according to an exemplary embodiment in the present disclosure.

FIG. 10 is a cross-sectional view illustrating an IC chip package which may be used in the biological information detecting apparatus according to an exemplary embodiment in the present disclosure.

Referring to FIG. 10, it may be understood that an IC chip package 100B according to the present exemplary embodiment has a structure similar to that illustrated in FIGS. 1, 3, and 4 except that an antenna pattern 142A is disposed on the same level as the redistribution layer 142. Components according to the present exemplary embodiment may be understood with reference to the description for the same or similar components of the IC chip package 100A illustrated in FIGS. 1, 3, and 4, unless explicitly described to the contrary.

Unlike the exemplary embodiment described above, the IC chip package 100B according to the present exemplary embodiment includes the antenna pattern 142A having a coil form and formed by the same process as that of a redistribution layer 142. The antenna pattern 142A may be connected to a connection pad 120P of an IC chip 120 through first and second feeding lines 142F1 and 142F2 disposed on the same level as the redistribution layer 142. In addition, the first wiring layer 112*a* disposed on the first surface 110A of the frame 110 may be provided as a ground layer 112*a*G.

Figure 11A:
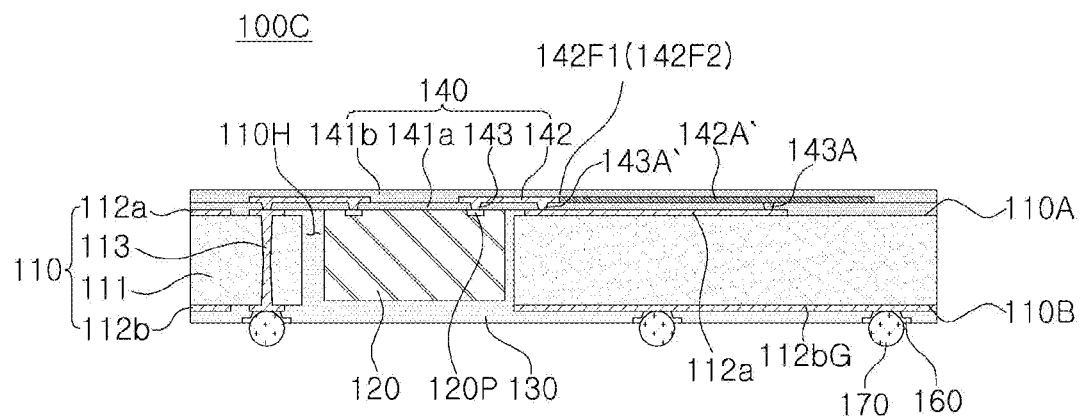
Figure 11B:
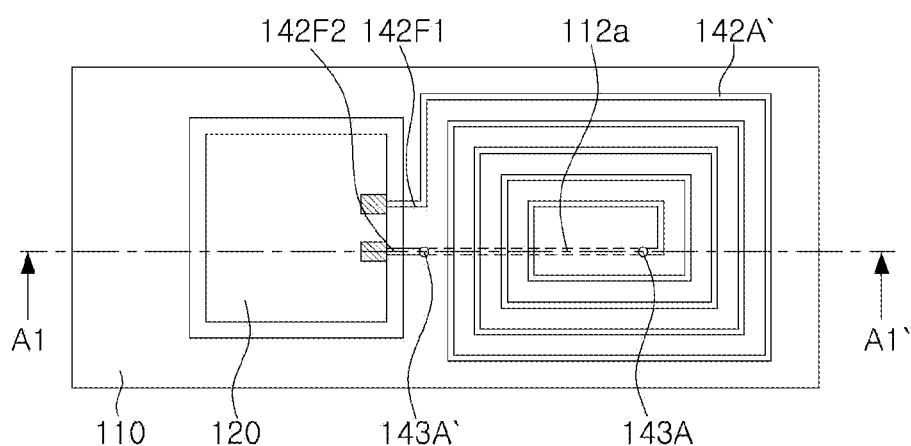
FIG. 11B is a plan view illustrating an antenna pattern used in the IC chip package of FIG. 11A.

FIGS. 11A and 11B are, respectively, a cross-sectional view and a plan view illustrating an IC chip package which may be used in the biological information detecting apparatus according to an exemplary embodiment in the present disclosure. The plan view of FIG. 11B is a schematic plan view mainly illustrating an antenna pattern, and FIG. 11A illustrates a cross section taken along line A1-A1' of FIG. 11B.

Referring to FIGS. 11A and 11B, it may be understood that an IC chip package 100C according to the present exemplary embodiment has a structure similar to that illustrated in FIG. 10 except that an antenna pattern 142A' has a coil form which is wound multiple times, and a second feeding line is connected to a first wiring layer 112*a* disposed on a different level. Components according to the present exemplary embodiment may be understood with reference to the description for the same or similar components of the IC chip packages 100A and 100B illustrated in FIGS. 1, 3, 4, and 10 unless explicitly described to the contrary.

The antenna pattern 142A' used in the present exemplary embodiment may be disposed on the same level as the redistribution layer 142, similarly to the exemplary embodiment illustrated in FIG. 10, and may have a coil form which is wound multiple times as illustrated in FIG. 11B. In detail, the antenna pattern 142A' may be wound multiple times from a first feeding line 142F1 so that an end portion of the antenna pattern 142A' is positioned at an inner side of the antenna pattern 142A'. The end portion of the antenna pattern 142A' may be connected to the first wiring layer 112*a* through a first via 143A, and the first wiring layer 112*a* may extend toward an IC chip 120, and an extended portion of the first wiring layer 112*a* may be connected to a second feeding line 142F2 through a second via 143A'. The first wiring layer 112a used in the present exemplary embodiment may be provided on a first surface 110A of a frame and have a line form as illustrated in FIG. 11B.

Figure 12A:
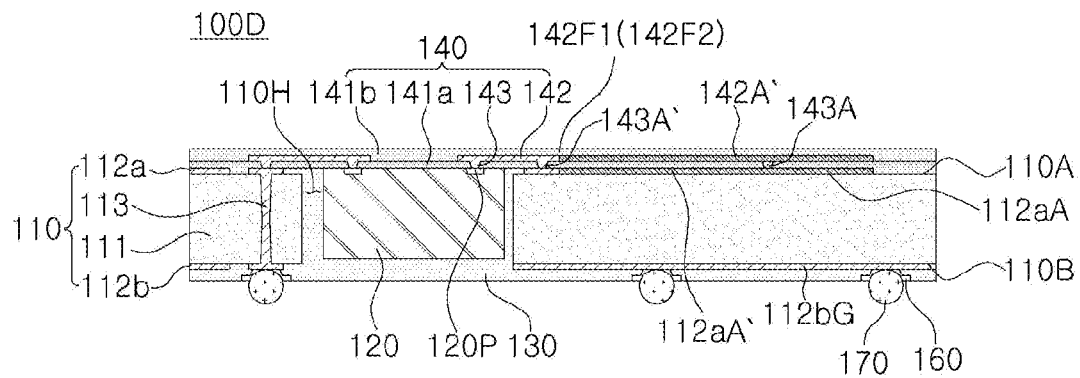
Figure 12B:
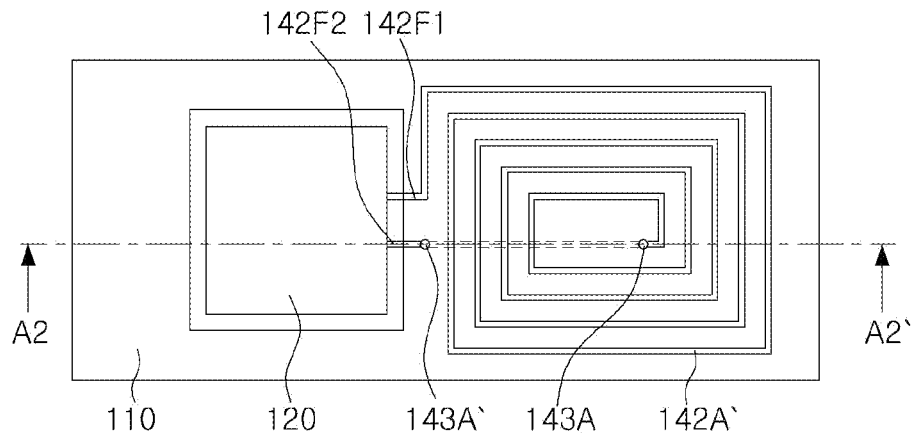
FIGS. 12B and 12C are, respectively, plan views illustrating antenna patterns used in the IC chip package of FIG. 12A.
Figure 12C:
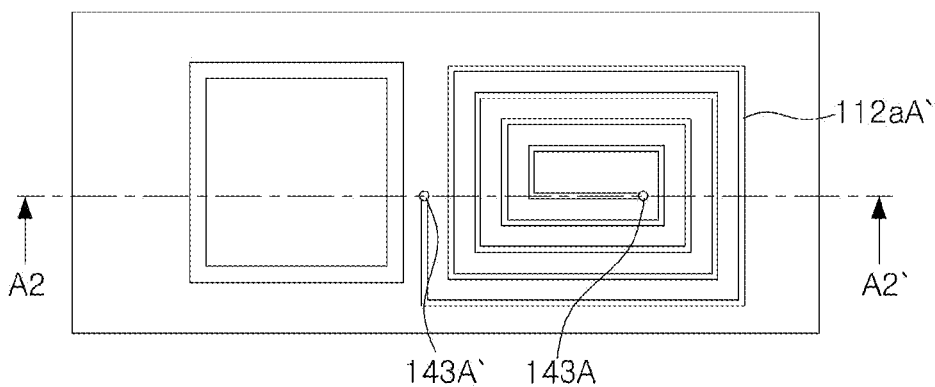

FIGS. 12A through 12C are, respectively, a cross-sectional view and plan views illustrating an IC chip package which may be used in the biological information detecting apparatus according to an exemplary embodiment in the present disclosure. The plan views of FIGS. 12B and 12C are schematic views mainly illustrating an antenna pattern when viewed on different levels, and FIG. 12A illustrates a cross section taken along line A2-A2' of FIGS. 12B and 12C.

Referring to FIGS. 12A through 12C, it may be understood that an IC chip package 100D according to the present exemplary embodiment has a structure similar to that illustrated in FIGS. 11A and 11B except that the IC chip package 100D includes a first antenna pattern 142A' and a second antenna pattern 112aA' which are wound multiple times, respectively. Components according to the present exemplary embodiment may be understood with reference to the description for the same or similar components of the IC chip packages 100A, 100B, and 100C illustrated in FIGS. 1, 3, 4, 10, and 11A and 11B unless explicitly described to the contrary.

The antenna used in the present exemplary embodiment includes the first antenna pattern 142A' and the second antenna pattern 112aA' which are wound multiple times, respectively.

The first antenna pattern 142A' may be disposed on the same level as a redistribution layer 142, similarly to the antenna pattern 142A' illustrated in FIGS. 11A and 11B, and may have a coil form which is wound multiple times as illustrated in FIG. 12B. In detail, the first antenna pattern 142A' is wound multiple times from a first feeding line 142F1 so that an end portion of the first antenna pattern 142A' is positioned at an inner side of the first antenna pattern 142A'. The end portion of the first antenna pattern 142A' may be connected to the second antenna pattern 112aA' through a first via 143A. The second antenna pattern 112aA' may be disposed on a first surface 110A of a frame 110, and may have a coil form which is wound multiple times so that the second antenna pattern 112aA' expands outwardly as illustrated in FIG. 12C. An end portion of the second antenna pattern 112aA' may be connected to a second feeding line 142F2 through a second via 143A'. The first and second vias 143A and 143A' may penetrate through an insulating layer 141.

Figure 13A:
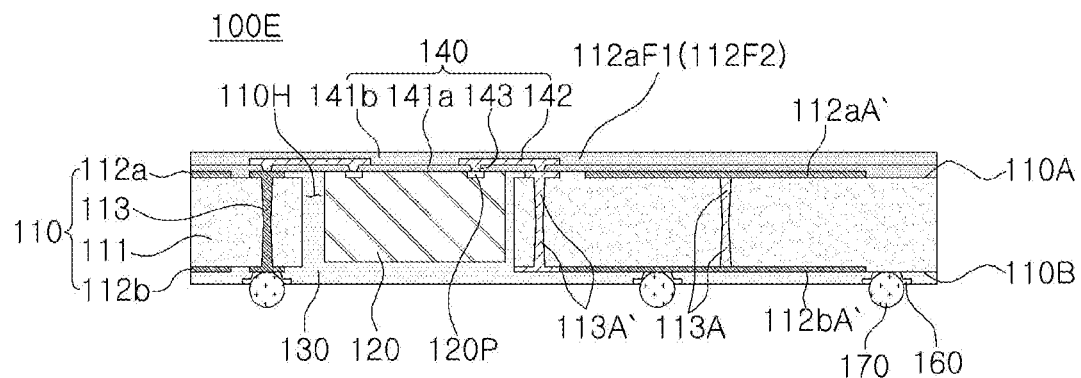
Figure 13B:
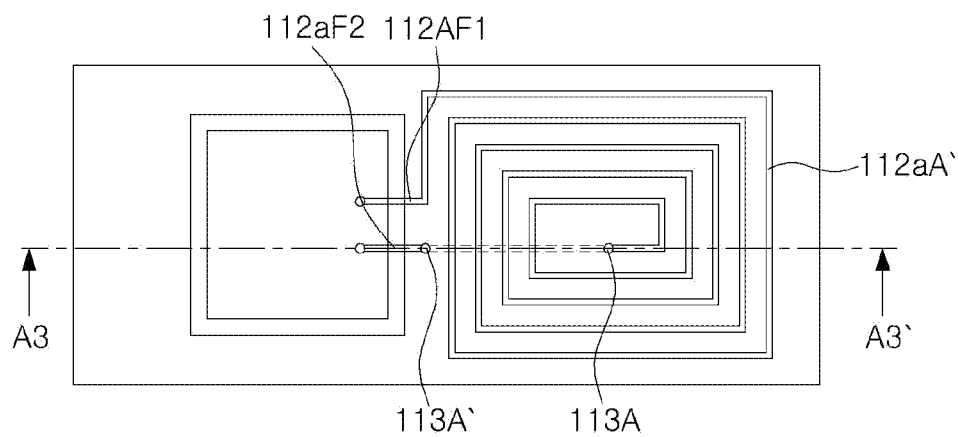
FIGS. 13B and 13C are, respectively, plan views illustrating antenna patterns used in the IC chip package of FIG. 13A.
Figure 13C:
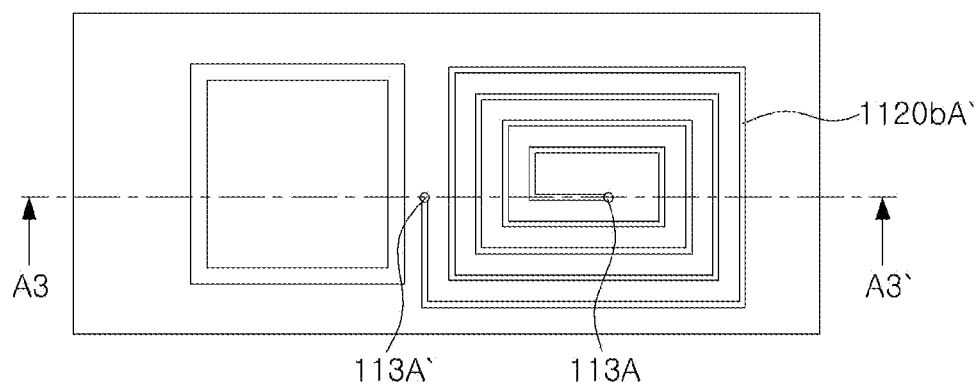

FIGS. 13A through 13C are, respectively, a cross-sectional view and plan views illustrating an IC chip package which may be used in the biological information detecting apparatus according to an exemplary embodiment in the present disclosure. The plan views of FIGS. 13B and 13C are schematic views mainly illustrating an antenna pattern when viewed on different levels, and FIG. 13A illustrates a cross section taken along line A3-A3' of FIGS. 13B and 13C.

Referring to FIGS. 13A through 13C, it may be understood that an IC chip package 100E according to the present exemplary embodiment has a structure similar to that illustrated in FIGS. 11A and 11B except that the IC chip package 100E includes a first antenna pattern 112aA' and a second antenna pattern 112bA' which are disposed on first and second surfaces 110A and 110B of a frame 110, respectively. Components according to the present exemplary embodiment may be understood with reference to the description for the same or similar components of the IC chip packages 100A, 100B, 100C, and 100D illustrated in FIGS. 1, 3, 4, 10, 11A and 11B, and 12A through 12C, unless explicitly described to the contrary.

The antenna used in the present exemplary embodiment includes the first antenna pattern 112aA' and the second antenna pattern 112bA' which are wound multiple times and disposed on the first and second surfaces 110A and 110B of the frame 110, respectively.

The first antenna pattern 112aA' may be disposed on the first surface 110A of the frame 110, similarly to the antenna pattern 112aA' illustrated in FIG. 12B, and may have a coil form which is wound multiple times inwardly from a first feeding line 142F1 as illustrated in FIG. 13B. An end portion of the first antenna pattern 112aA' may be connected to the second antenna pattern 112bA' through a first through via 113A. The second antenna pattern 112bA' may be disposed on the second surface 110B of the frame 110, and may have a coil form which is wound multiple times so that the second antenna pattern 112aA' expands outwardly as illustrated in FIG. 12C. An end portion of the second antenna pattern 112bA' may be connected to a second feeding line 142F2 through a second through via 113A'. The first and second through vias 113A and 113A' may penetrate through an insulating layer 111 of the frame 110.

The biological information detecting apparatus according to the present exemplary embodiment may be implemented in various forms. The biological information detecting apparatus may be various modified depending on a coupling form of the LC resonant pressure sensor and the IC chip package (see FIGS. 14 through 16).

Figure 14:
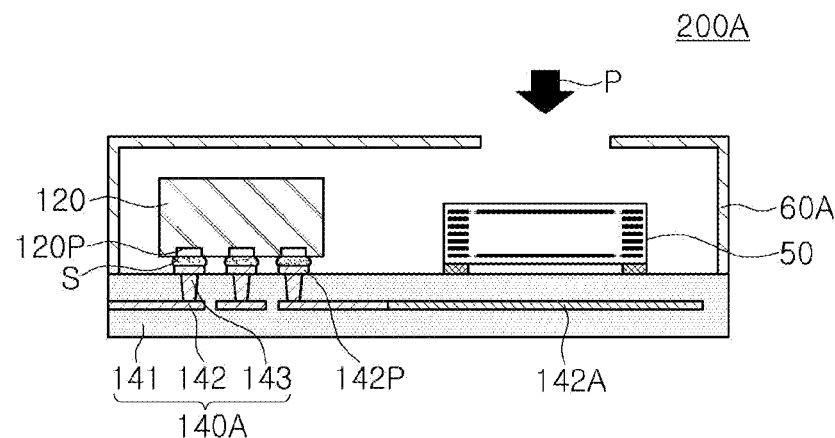
FIGS. 14 through 16 are schematic cross-sectional views illustrating biological information detecting devices according to various exemplary embodiments in the present disclosure.

FIG. 14 is a cross-sectional view schematically illustrating a biological information detecting apparatus according to an exemplary embodiment in the present disclosure.

Referring to FIG. 14, a biological information detecting apparatus 200A according to the present exemplary embodiment may include a connection structure 140A, and an IC chip 120 and an LC resonant pressure sensor 50 which are mounted on an upper surface of the connection structure 140A. The biological information detecting apparatus 200A may include a housing 60A disposed on the upper surface of the connection structure 140.

A connection pad 120P of the IC chip 120 may be connected to a bonding pad 142P by using a connection metal S such as a solder, and the bonding pad 142P may be connected to a redistribution layer 142 through a via 143. The connection structure 140 may include an antenna pattern 142A having a coil form connected to the redistribution layer 142 and the antenna pattern 142A may be disposed to overlap the LC resonant pressure sensor 50 in a plan view of the apparatus 200A.

Figure 15:
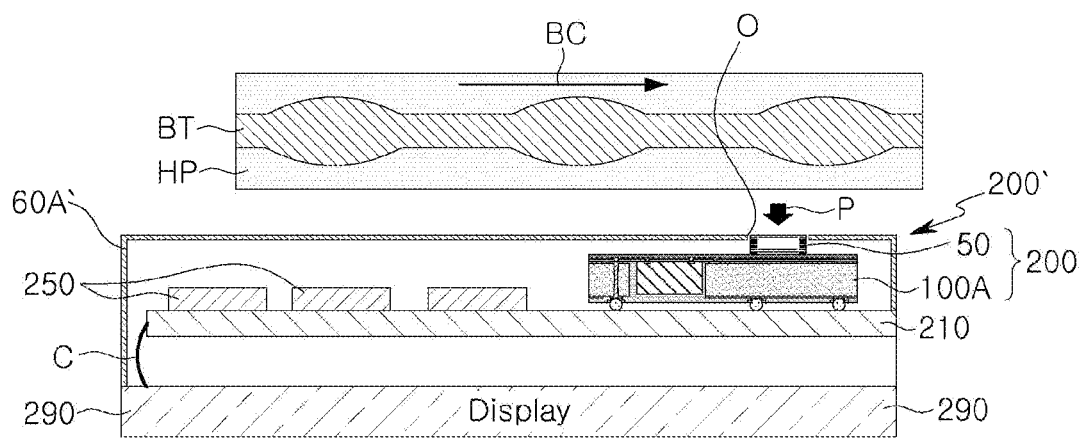

FIG. 15 is a cross-sectional view schematically illustrating a biological information detecting apparatus according to an exemplary embodiment in the present disclosure.

Referring to FIG. 15, a biological information detecting apparatus 200' according to the present exemplary embodiment may include a mainboard 210 such as a printed circuit board, an assembly of the IC chip package 100A illustrated in FIG. 1 and an LC resonant pressure sensor 50, an electronic component 250, and a housing 60A' covering an upper surface of the mainboard 210, the assembly and the electronic component 250 being mounted on the upper surface of the mainboard 210. The housing 60A' may include an opening O disposed in a region corresponding to the LC resonant pressure sensor 50 so that an external pressure may be detected. The biological information detecting apparatus 200' may further include a display 290 connected to the mainboard 210 by a metal line C and displaying biological information detected by the IC chip.

Figure 16:
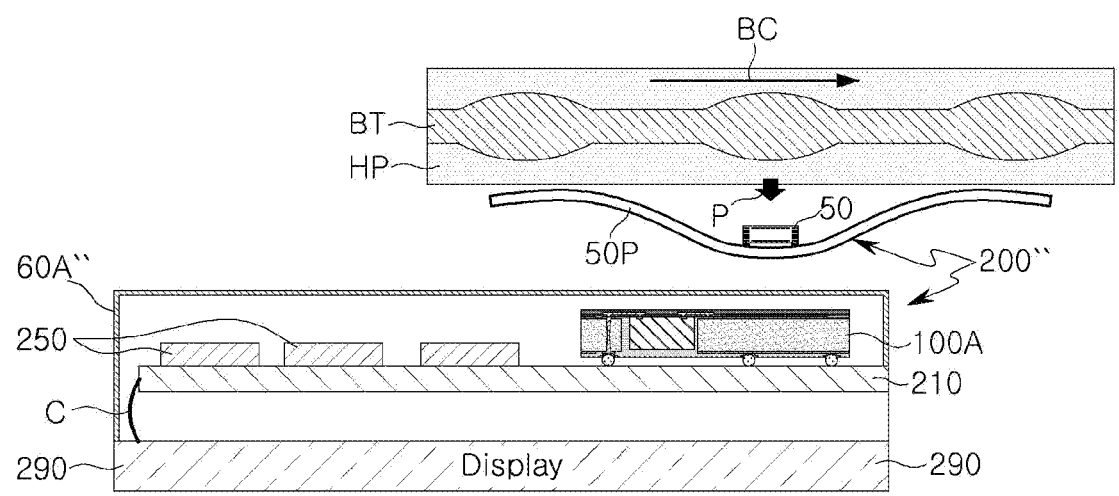

FIG. 16 is a cross-sectional view illustrating a biological information detecting apparatus according to an exemplary embodiment in the present disclosure.

Referring to FIG. 16, a biological information detecting apparatus 200" according to the present exemplary embodiment may include a mainboard 210 such as a printed circuit board, the IC chip package 100A illustrated in FIG. 1, an electronic component 250, and a housing 60A" covering an upper surface of the mainboard 210, the IC chip package 100A and the electronic component 250 being mounted on the upper surface of the mainboard 210. The biological information detecting apparatus 200" may further include a display 290 connected to the mainboard 210 by a metal line C and displaying biological information detected by the IC chip. These components constitute one main body.

The biological information detecting apparatus 200" according to the present exemplary embodiment may include an LC resonant pressure sensor 50 separately from the main body described above. As such, in the present exemplary embodiment, the LC resonant pressure sensor 50 may be provided separately from the IC chip package 100A. The LC resonant pressure sensor 50 may be attached on a surface of a human body (HP) as a measurement target by using a bonding patch 50P. When measuring biological information, the main body may be moved so that an antenna portion of the IC chip package 100A overlaps the LC resonant pressure sensor 50 in a plan view of the IC chip package 100A, and in this state, the biological information may be measured on the basis of a change in a power transmission rate according to a resonance principle described above.

As set forth above, according to the exemplary embodiment in the present disclosure, the LC resonant pressure sensor and the IC chip package may be combined with each other and a change in resonance frequency caused by an external pressure such as heartbeat and a change in a power transmission rate caused by the change in the resonance frequency may be used, thereby providing the compact biological information (for example, a heart rate) detecting apparatus.

Herein, a lower side, a lower portion, a lower surface, and the like, are used to refer to a downward direction in relation to cross sections of the drawings for convenience, while an upper side, an upper portion, an upper surface, and the like, are used to refer to an opposite direction to the downward direction. However, these directions are defined for convenience of explanation, and the claims are not particularly limited by the directions defined as described above.

While exemplary embodiments have been shown and described above, it will be apparent to those skilled in the art that modifications and variations could be made without departing from the scope of the present invention as defined by the appended claims.

What is claimed is:

1. A biological information detecting apparatus comprising:
    an LC resonant pressure sensor including a resonant circuit including a capacitor and an inductor, and having a resonant frequency that changes depending on a change in external pressure applied to the capacitor; and
    an integrated circuit (IC) chip package including an antenna radiating a radio frequency (RF) signal within a preset frequency band, wherein a change in the resonant frequency results in a change in a power transmission rate depending on a matching rate between the resonant frequency and a frequency of the RF signal,
    wherein the IC chip package includes:
    the antenna disposed in a region overlapping at least a portion of the LC resonant pressure sensor in a plan view of the IC chip package;
    a connection structure including a redistribution layer connected to the antenna; and
    an IC chip disposed on one surface of the connection structure, connected to the redistribution layer, and configured to detect biological information on the basis of the change in the power transmission rate.

2. The biological information detecting apparatus of claim 1, wherein the antenna includes a coil pattern disposed on a same level as the redistribution layer disposed in the connection structure with respect to a stacking direction.

3. The biological information detecting apparatus of claim 2, wherein the coil pattern is connected to the redistribution layer and connection pads of the IC chip by feeding lines protruding from one side of the antenna for signal connections.

4. The biological information detecting apparatus of claim 1, wherein the redistribution layer includes a plurality of redistribution layers disposed on different levels with respect to a stacking direction, and
    the antenna includes a plurality of coil patterns respectively disposed on same levels as the plurality of redistribution layers, and at least one via connecting the plurality of coil patterns to each other.

5. The biological information detecting apparatus of claim 1, wherein the IC chip package further includes a frame having a first surface on which the connection structure is disposed and a second surface opposing the first surface, the frame having a cavity in which the IC chip is accommodated and an encapsulant encapsulating the IC chip and covering the second surface of the frame.

6. The biological information detecting apparatus of claim 5, wherein the antenna includes a coil pattern disposed on the first surface of the frame.

7. The biological information detecting apparatus of claim 5, wherein the antenna includes first and second coil patterns disposed on the first and second surfaces of the frame, respectively, and a through via penetrating through the frame and connecting the first and second coil patterns to each other.

8. The biological information detecting apparatus of claim 5, wherein the antenna includes a coil pattern disposed on the first surface of the frame, and the IC chip package further includes a ground pattern disposed on the second surface of the frame in a region overlapping the coil pattern in the plan view.

9. The biological information detecting apparatus of claim 5, wherein the frame includes a first wiring layer disposed on the first surface and connected to the redistribution layer, a second wiring layer disposed on the second surface, and a via penetrating through the frame and connecting the first and second wiring layers to each other.

10. The biological information detecting apparatus of claim 9, wherein thicknesses of the first and second wiring layers of the frame are greater than that of the redistribution layer of the connection structure.

11. The biological information detecting apparatus of claim 9, wherein the IC chip package includes an underbump metal (UBM) layer disposed on the encapsulant and connected to the second wiring layer, and an electrical connection metal disposed on the underbump metal layer.

12. The biological information detecting apparatus of claim 1, wherein the biological information includes a heart rate, and the IC chip package is configured to count the number of peaks in the change in the power transmission rate within a predetermined time to detect the heart rate.

13. The biological information detecting apparatus of claim 1, wherein the LC resonant pressure sensor, having a microelectromechanical system (MEMS) structure, includes a coil pattern defining the inductor and electrode patterns defining the capacitor, the electrode patterns disposed at an inner side of the coil pattern and having a predetermined interval between the electrode patterns.

14. A biological information detecting apparatus comprising:
an LC resonant pressure sensor including a resonant circuit including a capacitor and an inductor, and having a resonant frequency that changes depending on a change in external pressure applied to the capacitor; and
an integrated circuit (IC) chip package including an antenna radiating a radio frequency (RF) signal within a preset frequency band, wherein a change in the resonant frequency results in a change in a power transmission rate depending on a matching rate between the resonant frequency and a frequency of the RF signal,
wherein the IC chip package includes:
a frame having first and second surfaces opposing each other and having a cavity;
a connection structure disposed on the first surface of the frame and including a redistribution layer;
an IC chip accommodated in the cavity, connected to the redistribution layer, and detecting biological information on the basis of the change in the power transmission rate; and
an encapsulant encapsulating the IC chip and covering the second surface of the frame, and
wherein the antenna is disposed on at least one of the connection structure or the first surface of the frame, and connected to the redistribution layer.

15. The biological information detecting apparatus of claim 14, wherein the LC resonant pressure sensor is disposed on the connection structure to overlap the antenna in a plan view of the IC chip package, and is coupled with the IC chip package.

16. The biological information detecting apparatus of claim 14, wherein the LC resonant pressure sensor is provided separately from the IC chip package and includes a bonding patch for being attached to a measurement target.

17. The biological information detecting apparatus of claim 14, wherein the frame includes a wiring structure connecting the first and second surfaces to each other and connected to the redistribution layer, and the IC chip package includes an underbump metal layer disposed on the encapsulant and connected to the wiring structure, and an electrical connection metal disposed on the underbump metal layer.

18. The biological information detecting apparatus of claim 14, further comprising a display displaying the biological information detected by the IC chip.

* * * * *